(12) United States Patent
Andersen

(10) Patent No.: US 8,275,463 B1
(45) Date of Patent: Sep. 25, 2012

(54) RECORDING A CONTEXT FOR SENSED BIOLOGICAL DATA

(75) Inventor: Dean Andersen, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1325 days.

(21) Appl. No.: 11/670,328

(22) Filed: Feb. 1, 2007

(51) Int. Cl.
 *A61N 1/08* (2006.01)
(52) U.S. Cl. ............... 607/59; 607/32; 607/30
(58) Field of Classification Search .............. 607/30–32, 607/59, 60; 128/903
 See application file for complete search history.

(56) References Cited

U.S. PATENT DOCUMENTS

| | | | |
|---|---|---|---|
| 5,113,869 A * | 5/1992 | Nappholz et al. ............. 600/508 |
| 5,135,004 A | 8/1992 | Adams et al. |
| 5,156,148 A | 10/1992 | Cohen |
| 5,199,428 A | 4/1993 | Obel et al. |
| 5,203,326 A | 4/1993 | Collins |
| 5,313,953 A | 5/1994 | Yomtov et al. |
| 5,324,315 A * | 6/1994 | Grevious ........................ 607/60 |
| 5,497,780 A | 3/1996 | Zehender |
| 5,531,768 A | 7/1996 | Alferness |
| 5,669,391 A | 9/1997 | Williams |
| 5,725,559 A * | 3/1998 | Alt et al. ............................ 607/5 |
| 5,732,708 A | 3/1998 | Nau et al. |
| 6,016,443 A | 1/2000 | Ekwall et al. |
| 6,021,350 A | 2/2000 | Mathson |
| 6,061,793 A * | 5/2000 | Tewfik et al. .................. 713/176 |
| 6,108,577 A | 8/2000 | Benser |
| 6,112,116 A | 8/2000 | Fischell et al. |
| 6,115,628 A | 9/2000 | Stadler et al. |
| 6,128,526 A | 10/2000 | Stadler et al. |
| 6,233,486 B1 | 5/2001 | Ekwall et al. |
| 6,256,538 B1 | 7/2001 | Ekwall |
| 6,264,606 B1 | 7/2001 | Ekwall et al. |
| 6,272,379 B1 | 8/2001 | Fischell et al. |
| 6,368,284 B1 | 4/2002 | Bardy |
| 6,381,493 B1 | 4/2002 | Stadler et al. |
| 6,468,263 B1 | 10/2002 | Fischell et al. |
| 6,501,983 B1 | 12/2002 | Natarajan et al. |
| 7,066,891 B2 | 6/2006 | Stadler et al. |
| 2002/0059520 A1 * | 5/2002 | Murakami et al. ............ 713/176 |
| 2002/0143262 A1 | 10/2002 | Bardy |
| 2004/0116981 A1 * | 6/2004 | Mazar ............................ 607/60 |
| 2004/0133247 A1 | 7/2004 | Stahmann |
| 2006/0161224 A1 * | 7/2006 | Samuelsson et al. ........... 607/60 |
| 2006/0173498 A1 * | 8/2006 | Banville et al. .................. 607/5 |

* cited by examiner

*Primary Examiner* — Scott Getzow
*Assistant Examiner* — Hiba El-Kaissi
(74) *Attorney, Agent, or Firm* — Steven M. Mitchell

(57) ABSTRACT

Exemplary techniques for recording a context for sensed biological data are described. One technique senses biological data from a patient and records supporting data with the sensed biological data.

23 Claims, 8 Drawing Sheets

RECORDING A CONTEXT FOR SENSED BIOLOGICAL DATA

FIELD OF THE INVENTION

The subject matter presented herein generally relates to recording a context for sensed biological data.

BACKGROUND

Various devices exist for sensing biological data from a patient. This sensed biological data can relate to any aspect of a patient's condition such as body temperature, respiration, activity, blood chemistry, electrical heart activity, etc. The sensed biological data is sensed in a particular context (i.e., from a particular patient by a particular device). Knowing information about the context enhances the diagnostic value of the sensed biological data. Supporting data relates to the particular context in which the sensed biological data is obtained. For instance consider a scenario involving an implantable medical device (IMD) employed to sense biological data related to heart function from an individual patient. Clinical data regarding the individual patient, such as the patient's age and the patient's sex, can contribute to the context. IMDs can sense large amounts of biological data relating to heart function, patient activity, thoracic impedance, etc. One aspect of heart function can be sensed as intracardiac electrogram (IEGM) data. The IEGM data is sensed with sensors that are adjusted for various settings or parameters such as sensitivity, amplification and filter characteristics. Further, the sensed biological data may be delivered from the sensor to the IMD which may further process the data, such as by an analog-to-digital conversion, according to its own internal settings. The settings of the sensor and/or the IMD can contribute to the context of the sensed biological data.

Often, some or all of the sensed biological data is subsequently downloaded from the patient and analyzed to diagnose a patient condition(s). Knowing the context in which the biological data was sensed can enhance the diagnostic value of the sensed biological data. For instance, a sensitivity setting on the IMD will affect whether a P-wave recorded in the IEGM data is actually a P-wave or some other cardiac event, such as a ventricular event.

Presently only rudimentary techniques are employed to associate context with the biological data. For instance, when biological data is downloaded from an IMD, extra process steps can be taken to also download at least some supporting data in a separate process. A clinician can create a data table to cross-reference the biological data and the supporting data. The clinician can enter and save the supporting data and cross-reference the supporting data to the biological data utilizing the data table. These techniques rely on human involvement to complete the data table and enter the supporting data, which may be accomplished on only a limited scale or not at all. Further, the data table and/or the supporting data may be lost at some point. In some cases, other clinicians accessing the sensed biological data may not know of the existence of the data table and/or the supporting data and/or the clinicians may be unable to locate the data tables and/or the supporting data. Often, the end result is that the context of the biological data is effectively unknown or only partially known. Improved techniques for associating biological data with its contextual supporting data could improve patient care at a micro-level and forward research knowledge at a macro-level.

SUMMARY

Exemplary techniques and systems for recording a context for sensed biological data are described. For example, one technique senses biological data from a patient and records supporting data with the sensed biological data.

In another example, an exemplary device includes means for sensing biological data from a patient. The device also includes means for generating a data file containing both the sensed biological data and supporting data relating to the sensed biological data.

In general, the various techniques, methods, devices, systems, etc., described herein, and equivalents thereof, are optionally suitable for recording a context for sensed biological data.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements wherever feasible.

Overview

Various exemplary techniques, methods, devices, systems, etc., described herein pertain to recording a context for sensed biological data. Medical devices, such as implantable medical devices (IMDs) sense or gather biological data from a patient. This sensed biological data can relate to any type of patient condition. For instance, the sensed biological data can relate to electrical heart activity, such as can be manifest as intracardiac electrogram (IEGM) data, thoracic impedance data, patient activity data, blood pressure data, respiration rate and/or volume data, blood chemistry data, and neurological activity data, among others.

The sensed biological data is sensed in a particular context (i.e., from a particular patient by a particular device). Knowing information about the context enhances the diagnostic value of the sensed biological data. Supporting (or support)

data relates to the particular context in which the sensed biological data is sensed. Stated another way, supporting data relates to conditions associated with sensing biological data. For example, the supporting data can convey information about a medical device that sensed the biological data. The supporting data can alternatively or additionally relate to clinical information about the patient from which the biological data was sensed. For example, the supporting data can convey patient information, such as the patient age and patient sex, among others.

The described implementations serve to record or otherwise preserve the sensed biological data with its context thereby enhancing the diagnostic value of the sensed biological data. Recording the supporting data with the sensed biological data reduces a likelihood of the supporting data getting separated from, and ultimately lost, such that the context of the sensed biological data is unknown.

In some of the implementations, the sensed biological data and its supporting data are manifest as a single data set. Either or both of the sensed biological data and its supporting data can be retrieved from the single data set as desired. One manifestation is to embed the supporting data onto the sensed biological data. In some cases the sensed biological data can be accessed and utilized with or without accessing the embedded supporting data. Yet, the embedded supporting data is available when desired.

First Exemplary System

Figure 1:
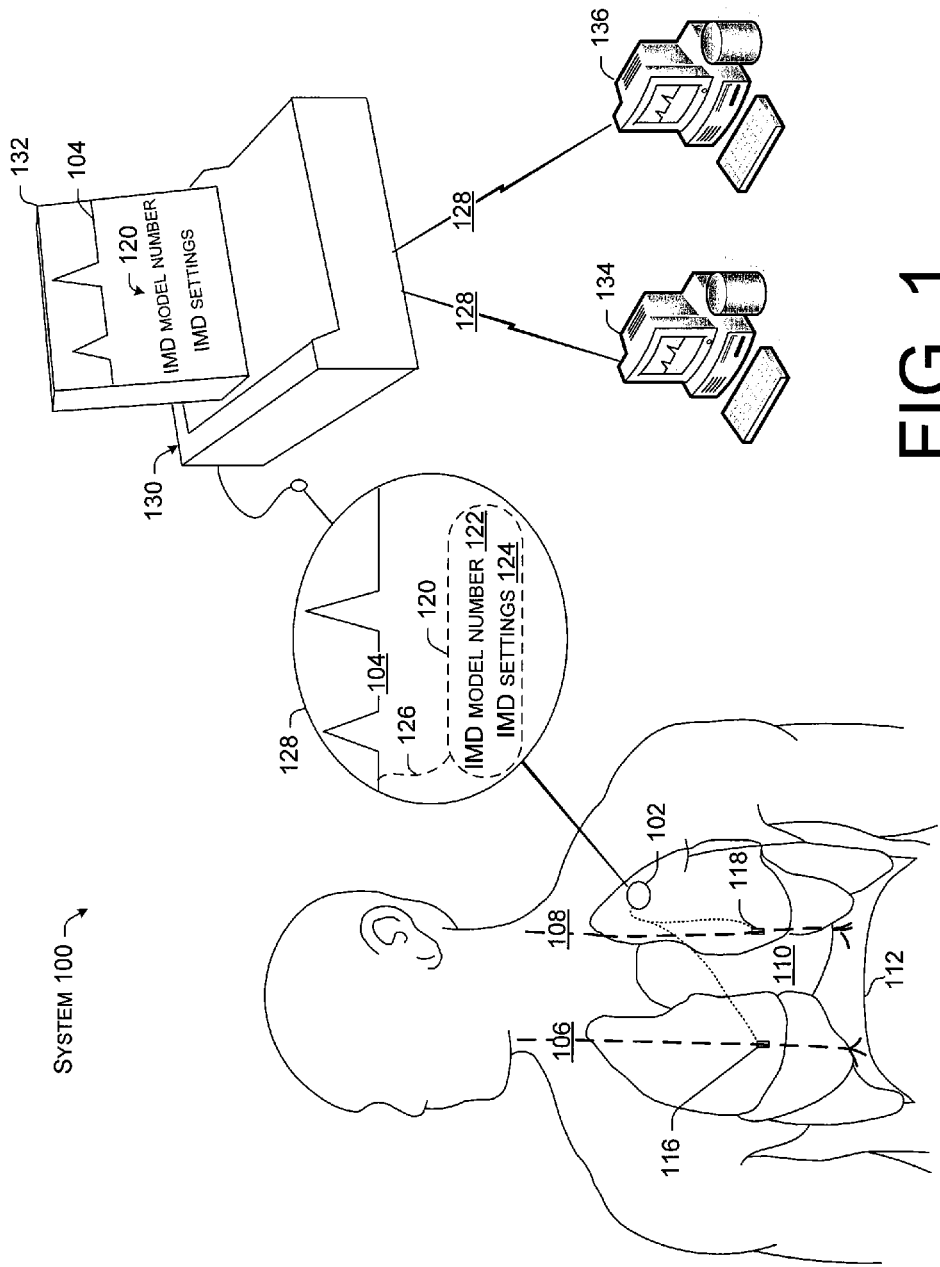
FIGS. 1-2 are simplified diagrams illustrating exemplary systems for recording a context for sensed biological data in accordance with one implementation.

FIG. 1 shows an exemplary system 100 for recording a context of sensed biological data. In this case, an implantable medical device (IMD) 102 is configured to sense biological data 104 in the form of sensed phrenic nerve activity data of the patient. In general, phrenic nerves 106 and 108 run from above the subclavian veins and down around the heart 110 (e.g., left and right side) to the surface of diaphragm 112. IMD 102 is coupled to the right phrenic nerve 106 via a first cuff electrode 116 and to the left phrenic nerve 108 via a second cuff electrode 118.

Phrenic nerve activity stimulates the patient's diaphragm 112 to contract. Contraction of the diaphragm 112 causes expansion of the thoracic cavity and ultimately produces an inhalation phase of the patient's respiratory cycle. Parameter values derived from sensed biological data 104 can be useful in determining the patient's respiratory rate and respiratory volume, among other uses. Possession of supporting data 120 can enhance the prognostic value of the sensed biological data 104 by conveying the context in which the biological data was sensed. For instance, all devices introduce some level of distortion into the sensed biological data. Knowing the type of device that sensed the biological data provides an opportunity for the distortion to be recognized and addressed. This knowledge can be utilized, for instance, to allow a more meaningful comparison between biological data sensed with one type of device and other biological data sensed with another type of device. In this case, the supporting data 120 includes an IMD model number 122 and IMD settings 124, such as sensitivity settings. The IMD settings can also include sample rate or other data about how and when the IMD acquires the biological data. Still other examples of supporting data can include data relating to the external environment of the patient. For instance, the supporting data can convey information about what healthcare facility the patient was at when the biological data was sensed and/or the identity of a clinician who was controlling the IMD such as via a programmer. In summary, supporting data can include any type of data that can enhance the usefulness of the biological data. Additional examples of supporting data are described above and below.

In this implementation, IMD 102 automatically records the supporting data 120 with the sensed biological data 104 as indicated logically at 126. In this case, the sensed biological data 104 and its supporting data 120 can be thought of as a single data set 128. The data set 128 can be downloaded to an external device, such as programmer 130 to convey both the supporting data and the sensed biological data. Various techniques can be employed to record the supporting data with its biological data. For instance, the supporting data can be annotated to the sensed biological data as one or more meta tags. In another scenario, the supporting data can be embedded on the sensed biological data. In one such case, the supporting data can be embedded at portions of the sensed biological data that are of relatively reduced prognostic value. Stated another way, the supporting data can be embedded on portions of the sensed biological data from which few or no parameter values are derived. Alternatively, the embedding can be performed generally uniformly along the sensed biological data. One technique of embedding the supporting data on the sensed biological data involves encoding the supporting data on the sensed biological data. One such scenario encodes the supporting data as what appears as 'white noise' which is then encoded onto the sensed biological data. An example of such a scenario involves digital watermarking where the supporting data is encoded onto the sensed biological data as a watermark. Examples employing watermarking to encode the supporting data onto the sensed biological data are described in more detail below in relation to FIGS. 2-5.

Returning to system 100, data set 128 includes both the sensed biological data 104 and the supporting data 120. The data set can be stored on IMD 102 and/or transmitted from the IMD to programmer 130. In some instances, external devices, such as programmer 130, can add additional supporting data to the data set 128 that conveys information about the external device, its environment, and/or its model number and settings, among others.

Data set 128 can be utilized at the programmer in many different ways. For instance, the programmer can utilize data set 128 in a traditional manner, such as to derive parameter values from the sensed biological data contained in data set 128. The sensed biological data 104 can also be displayed by programmer 130. Further, the programmer can access the data set's supporting data 120 to provide various enhanced functionalities. For instance, in the illustrated example of FIG. 1, programmer 130 has read supporting data 120 of data set 128 and is displaying both the sensed biological data 104 and the supporting data 120 on the programmer's display 132. In other scenarios the programmer can utilize the supporting data to normalize the sensed biological data in a manner which compensates for distortions of the sensed biological data inherent to the particular IMD model number 122 utilized to sense the biological data. Normalization allows more meaningful comparisons to biological data sensed by other IMD device types or models and/or to biological data sensed when the various IMD settings 124 are adjusted differently.

Further, programmer 130 can convey data set 128 to a plurality of computing devices 134, 136 without any concern that the data set's biological data and/or supporting data may become lost or separated from one another. The data set 128 can be stored by any or all of these devices (130, 134, and 136) as a single stand-alone data set that contains both the sensed biological data and its supporting data without referencing another data file. For example, no data tables need to be created and no entries of supporting data need to be made to preserve the association between the supporting data and the sensed biological data. The described implementations lend themselves to automation, so the sensed biological data's context is much more likely to be preserved than traditional scenarios that rely on human participation.

In other configurations, a downstream device, such as programmer 130, could receive the sensed biological data 104 and its supporting data 120 separately from the IMD 102. The downstream device could then record the supporting data on the sensed biological data to create a data set similar to data set 128. Such a configuration, while performant, increases a likelihood of the biological data and its supporting data becoming lost and/or separated before the recording is completed.

Second Exemplary System

Figure 2:
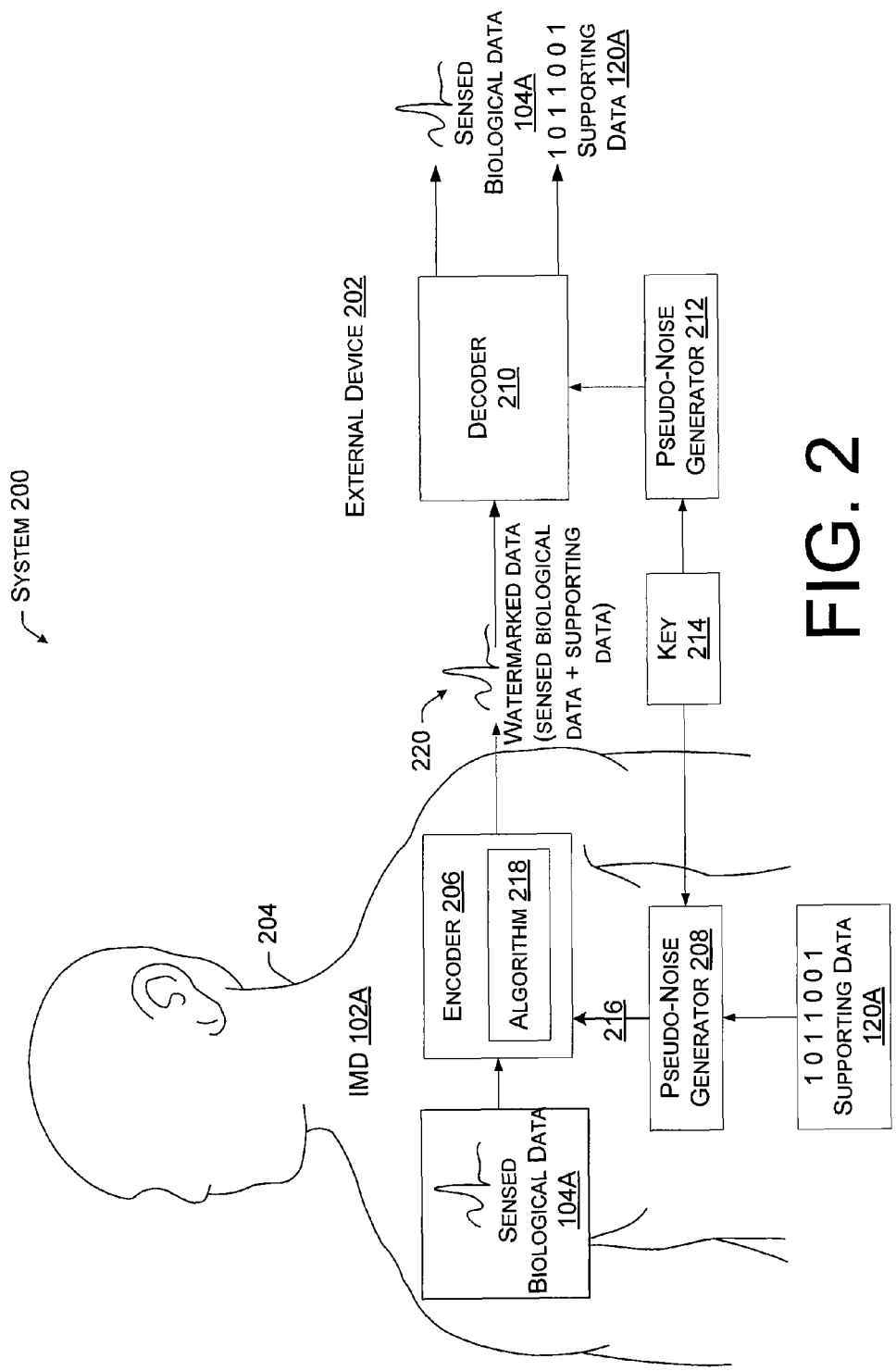
Figure 3:
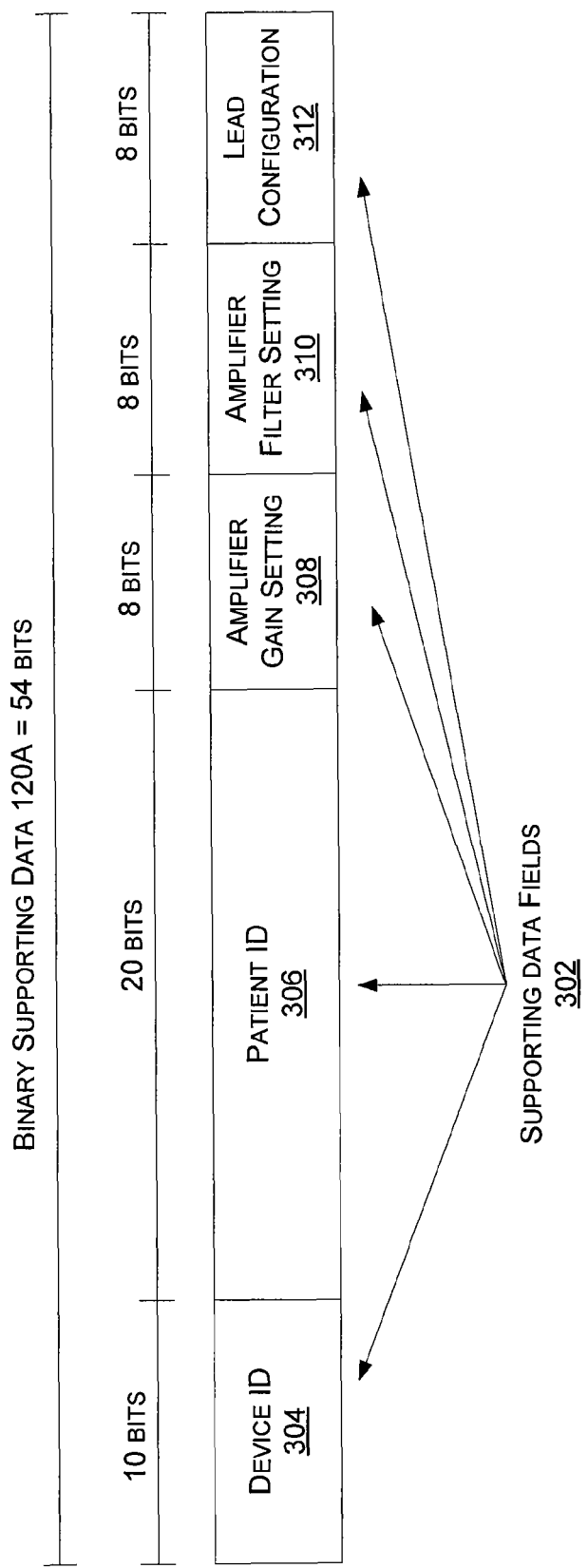
FIG. 3 illustrates exemplary supporting data for recording a context for sensed biological data in accordance with one implementation.

Collectively, FIGS. 2-5 illustrate examples of systems and associated techniques for embedding biological data with its supporting data via digital watermarking ("watermarking"). Watermarking embeds the supporting data on the sensed biological data through an encoding process. A watermarking system for encoding supporting data onto its biological data and for subsequently decoding the watermarked data is introduced in FIG. 2. FIG. 3 provides an example of supporting data that can be included in the watermark. The watermark encoding aspects are described in more detail in relation to FIG. 4 and the watermark decoding aspects are described in more detail in relation to FIG. 5.

FIG. 2 illustrates a particular watermark encoding/decoding system 200 that includes an IMD 102A and an external device 202. For the reader's convenience, the IMD's logical components are illustrated inside a patient outline 204 while the external device's components are illustrated outside outline 204. IMD 100A includes an encoder 206 and a pseudo-noise generator 208. External device 202 includes a decoder 210 and a pseudo noise generator 212. A key 214, which is a digital value, is utilized by both the IMD 102A and the external device 202 as will be described in more detail below.

Pseudo-noise generator 208 is operable to generate pseudo-noise sequences (designated with specificity in relation to FIG. 4) utilizing key 214. The pseudo-noise sequences are combined with the supporting data 120A to generate a pseudo-noise signal 216. Encoder 206 receives biological data 104A and the pseudo-noise signal 216. The encoder utilizes watermarking algorithm 218 to encode the pseudo-noise signal as a watermark onto the biological data 104A to produce watermarked data 220. Watermarked data 220 includes the sensed biological data and its supporting data encoded thereupon as a watermark. Stated another way, the watermark functions as a message carrier for the supporting data 120A that is encoded onto the biological data 104A resulting in watermarked data 220. Since the watermarked data 220 includes both the sensed biological data and its supporting data, the watermarked data can be stored in memory and/or communicated to external device 202 as a single stand-alone data file without needing to reference other data files to provide a context for the sensed biological data contained in the watermarked data.

While many suitable techniques can be employed in various implementations to record the context with the sensed biological data, digital watermarking offers several positive attributes. For instance, digital watermarking encodes the supporting data in the sensed biological data with relatively little impact to the sensed biological data. For example, watermarking can allow the sensed biological data to be analyzed in a traditional manner even when the supporting data is encoded onto the sensed biological data. So, for instance, relatively accurate parameter values can be obtained from the sensed biological data of the watermarked data without extracting the watermark. Also, watermarking offers a degree of security in that access to the supporting data can be controlled if desired via controlling access to key 214.

Assume for purposes of explanation that watermarked data 220 is communicated to external device 202. The external device can store the watermarked data 220 and/or analyze the sensed biological data of the watermarked data. For instance, the sensed biological data of the watermarked data can be analyzed to derive various parameter values even in the presence of the watermark. In such a case, the derived parameter values can be utilized in a known manner such as to determine a patient condition. Further, external device 202 can employ pseudo-noise generator 212 to separate or decode the watermarked data into the 'original' sensed biological data 104A and its supporting data 120A. Parameter values can then be derived from the sensed biological data. Key 214 allows the watermark (i.e., the supporting data) to be removed or extracted from the watermarked data 220 to restore the sensed biological data 104A. The key makes it possible to separate the supporting data from the pseudo-noise sequence so that the supporting data can be read.

FIG. 3 shows an example of how supporting data 120A can be encoded in binary form for use by the pseudo-noise generator 208 of FIG. 2. In this example, 54 bits are dedicated for supporting data 120A. The 54 bits are divided into five supporting data fields as indicated generally at 302. The five supporting data fields are designated as device ID 304, patient ID 306, amplifier gain setting 308, amplifier filter setting 310, and lead configuration 312. 10 bits of the 54 total bits are dedicated to device ID field 304, 20 bits to the patient ID field 306, 8 bits to the amplifier gain setting field 308, 8 bits to the amplifier filter setting field 310, and 8 bits to the lead configuration field 312. The skilled artisan should recognize that the total bits allocated for the supporting data, the number and identity of the fields, as well as their proportional allocation of the available bits are not critical and that a multitude of different configurations could be implemented that are consistent with the concepts described above and below.

Figure 4:
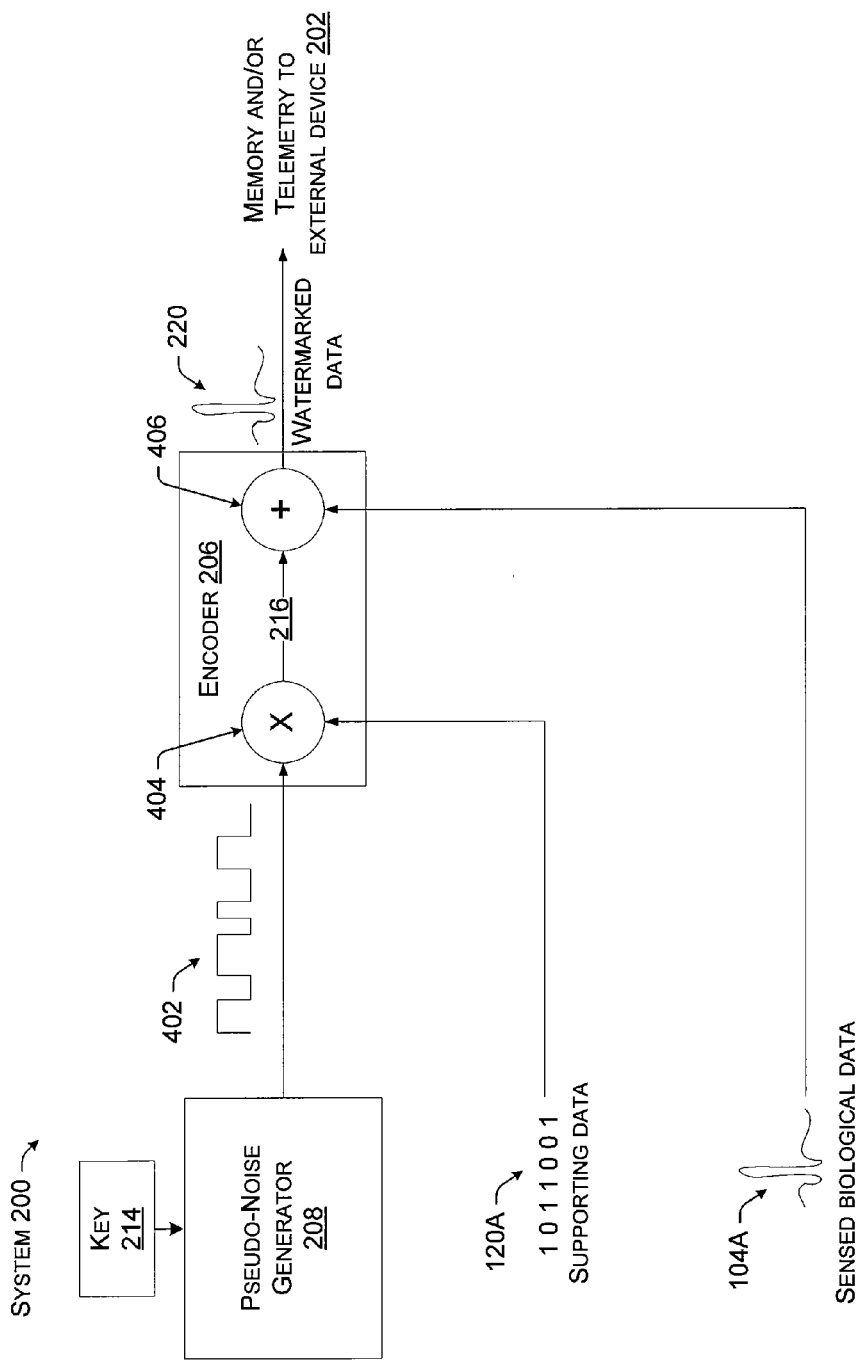
FIGS. 4-5 are simplified diagrams that illustrate portions of the system of FIG. 2 in more detail in accordance with one implementation.

FIG. 4 shows the encoding aspects of system 200 in more detail. In this instance, pseudo-noise generator 208 generates pseudo-noise sequence 402. The encoding technique multiplies pseudo-noise sequence 402 and the supporting data 120A at 404 to produce pseudo-noise signal 216. The pseudo-noise signal is then added as a watermark to the sensed biological data at 406 to produce watermarked data 220. The watermarked data can be stored on IMD 102A and/or communicated to external device 202.

In order to reduce degradation of the sensed biological data 104A within watermarked data 220, a watermark that reduces or minimizes alteration of the frequency spectrum of the sensed biological data can be desirable. Stated another way, the watermarked data 220 can have the general appearance of the sensed biological data 104A with a slight amount of white noise introduced into the sensed biological data. The presence of the white noise does not generally limit the usefulness of the sensed biological data 104A. Accordingly, in at least some implementations, parameter values derived from watermarked data 220 are generally equivalent to parameter values derived from the sensed biological data 104A.

Several classes of watermarks exist that can contain the supporting data 120A and that appear as relatively insignificant white noise when encoded onto the sensed biological data 104A. Pseudo-noise signals are an example of one of these classes of watermarking signals. Encoding the supporting data 120A as pseudo-noise signal 216 is useful in that it provides a relatively constant low-energy signal throughout the frequency spectrum except near the lowest frequencies. At the lowest frequencies there is little or no signal content. In this instance, by controlling an amount of energy of the pseudo-noise signal 216 during addition to the sensed biological data, the watermarked data can go almost unnoticeable relative to the unmarked sensed biological data 104A. Pseudo-noise generation provides but one example of a technique for generating a watermark that is relatively unnoticeable in the sensed biological data. Other watermark generating techniques can be utilized that may be more or less performant at generating a relatively unnoticeable watermark.

Figure 5:
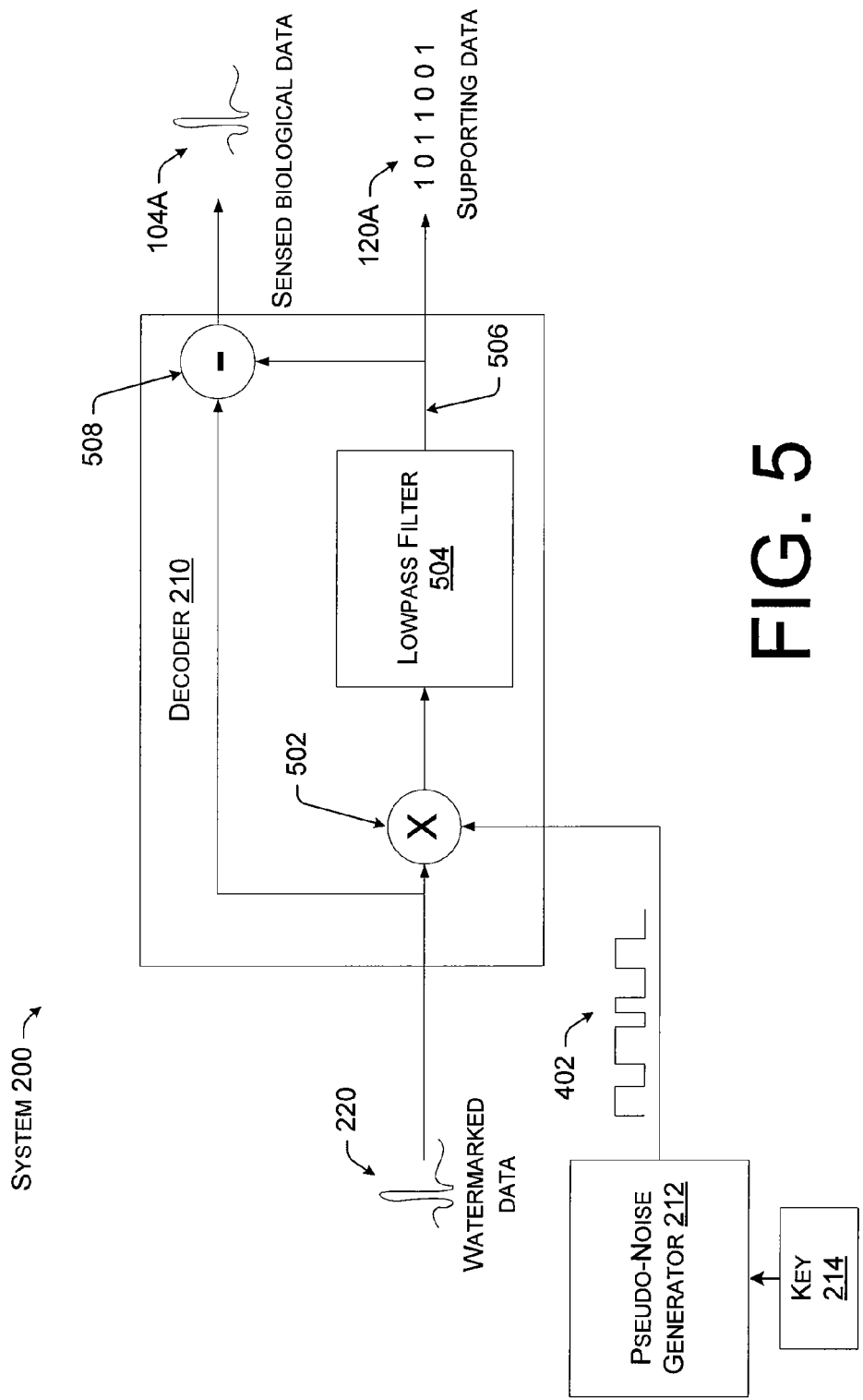

FIG. 5 shows the decoding aspects of system 200 in more detail. Watermark decoding serves to extract the watermark that was added to the sensed biological signal in the encoding process. In essence, the decoding process generates the same pseudo-noise sequence 402 by its own generator 212. The pseudo-noise sequence 402 is the same that was added to the biological data during the encoding process and the decoding process serves to subtract that pseudo-noise from the watermarked data 220. For instance, pseudo-noise generator 212 generates pseudo-noise signal 402 utilizing key 214. Pseudo-noise signal 402 is multiplied with the watermarked signal 220 at 502. The product is then sent through a low pass filter 504 to expose the watermark containing the supporting data 120A. The low pass filter is a transform that functions to allow low frequency signals to pass through and to block or attenuate high frequency signals. In this instance, low pass filter 504 blocks the sensed biological data and allows the supporting data 120A to be obtained at 506. The watermark is subtracted from the watermarked data 220 at 508 to obtain the original sensed biological data 104A. Collectively, these process (designated as 502 and 508) serve to obtain both the sensed biological data 104A and the supporting data 120A from watermarked data 220.

As mentioned above, configurations utilizing key 214 in the decoding process can offer several potential advantages. For instance, access to key 214 can be controlled, if desired, to limit access to the supporting data. Alternatively or additionally, such configurations provide a tamper detection or integrity functionality relative to the watermarked data 220. For example, consider a scenario where an unauthorized third party tampers with the watermarked data, such as by attempting to access the supporting data. The tampering can alter the digital sequence of the watermarked data so that when a subsequent authorized user or device attempts to decode the watermarked data with the key, the decoding process fails. Failure of the decoding process can indicate that the watermarked data is not in its original or expected form. In another instance, some portion of the watermarked data 220 may be lost, such as during a faulty transmission process. Likely, a subsequent authorized user/device will be unable to decode the watermarked data and will accordingly be made aware of the lack of integrity of the watermarked data. The watermarking process can also include a fingerprinting feature that serves to identify each device that subsequently access the watermarked data.

To summarize, FIGS. 2-5 provide an example where the supporting data is encoded as a watermark onto the biological data resulting in watermarked data. The watermarking process serves to encode the supporting data on the biological data in a manner that does not significantly diminish the usefulness of the sensed biological data. Stated another way, the supporting data becomes hidden as part of a signal conveying the biological data such that the presence of the supporting data is generally unnoticeable. Accordingly, the inclusion of the supporting data on the biological data leaves the biological data useful (i.e. a pattern that could be detected from the biological data prior to the supporting data being added can still be detected following the addition of the supporting data). The supporting data can subsequently be retrieved from the watermarked biological data when desired. Likewise, the supporting data can be extracted from the watermarked data to restore the sensed biological data. Parameter values can then be derived from the sensed biological data where the context in which the biological data was sensed is preserved in the supporting data. In many scenarios, the described techniques can be achieved automatically, without any human involvement, thereby further addressing the concerns described above.

FIGS. 2-5 provide but one non-limiting example for encoding supporting data onto sensed biological data as a watermark and subsequently decoding the watermark to obtain the supporting data and the sensed biological data in their original form. The skilled artisan should recognize many variations that are consistent with the concepts described above and below.

Exemplary Implantable Medical Device

Figure 6:
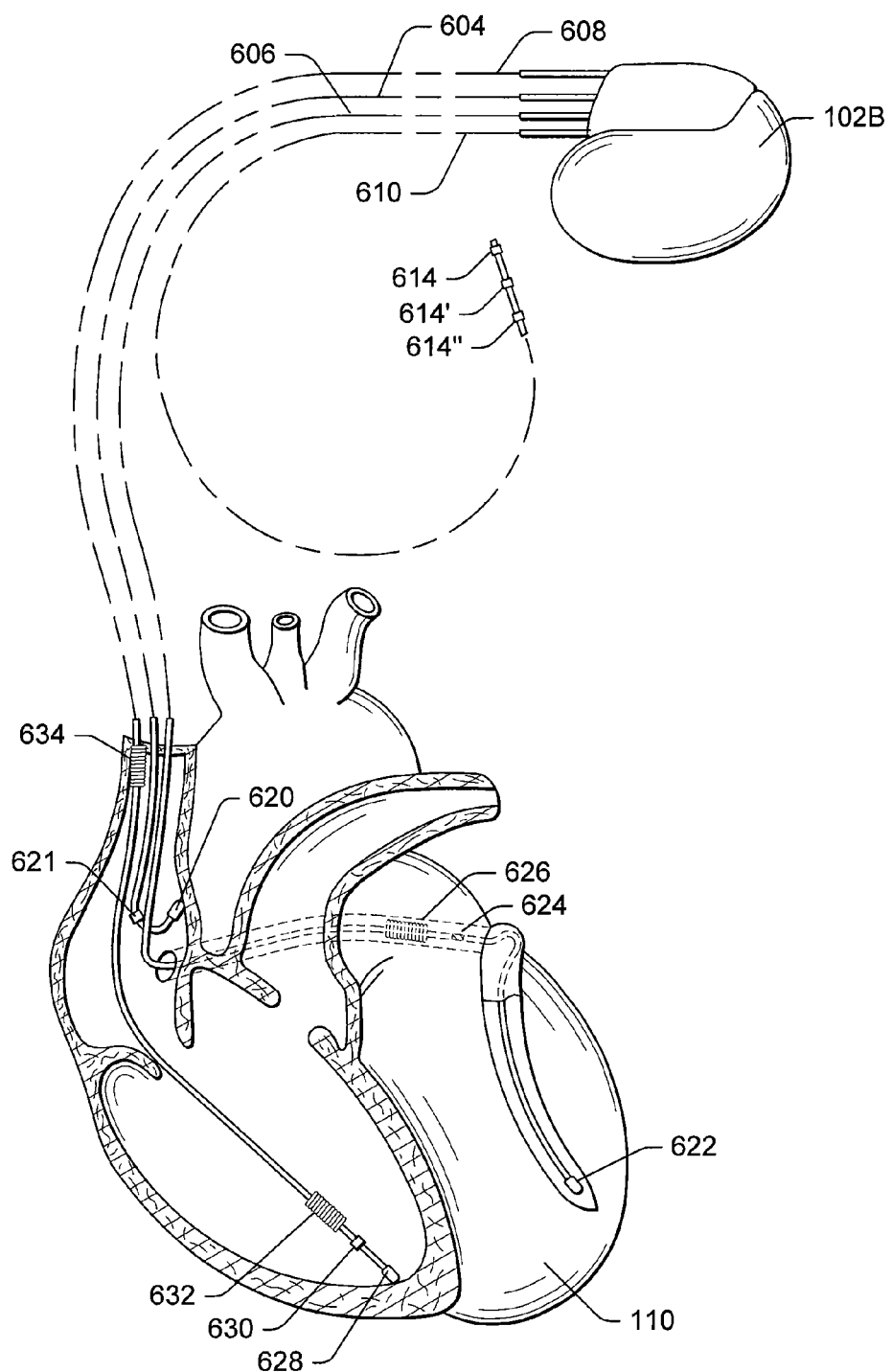
FIG. 6 is an illustration of an exemplary implantable medical device (IMD) for recording a context for sensed biological data in accordance with one implementation.
Figure 7:
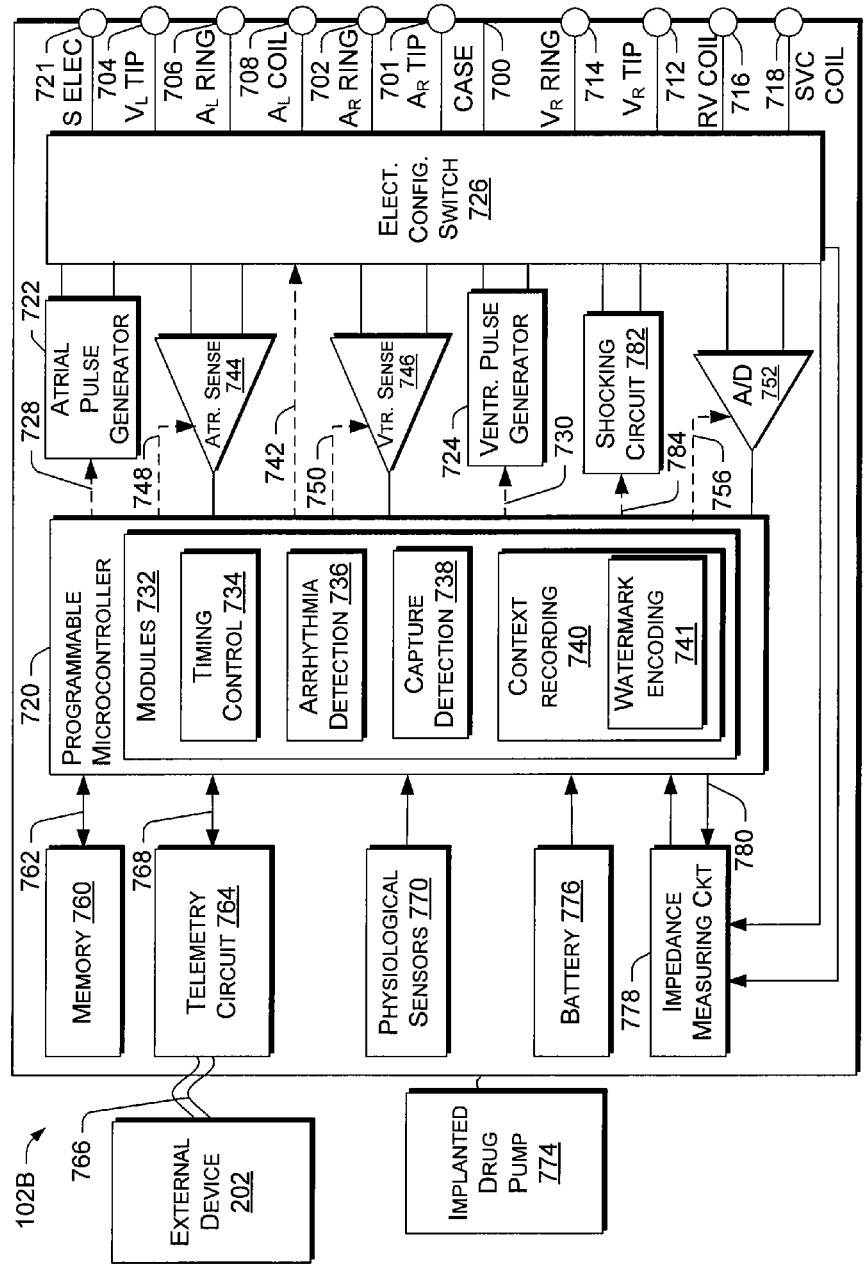
FIG. 7 is an illustration of block components of the exemplary IMD of FIG. 6 in accordance with one implementation.

The techniques described above and below can be implemented in connection with any IMD that is configured or configurable to sense or otherwise gather biological data from a patient. FIGS. 6-7 describe an IMD in the form of an implantable cardiac device (ICD) for sensing cardiac data and/or providing cardiac therapy. The principles described in relation to a cardiac device are equally applicable to other device configurations.

FIG. 6 shows an exemplary IMD 102B in electrical communication with a patient's heart 110 by way of three leads 604, 606, 608, suitable for delivering multi-chamber stimulation and shock therapy. The leads 604, 606, 608 are optionally configurable for delivery of stimulation pulses suitable for stimulation of autonomic nerves, non-myocardial tissue, other nerves, etc. In addition, IMD 102B includes a fourth lead 610 having, in this implementation, three electrodes 614, 614', 614" suitable for stimulation and/or sensing of autonomic nerves, non-myocardial tissue, other nerves, etc. For example, this lead may be positioned in and/or near a patient's heart or near an autonomic nerve within a patient's body and remote from the heart. In another example, the fourth lead can be configured to sense the phrenic nerve and/or activation of the diaphragm. The right atrial lead 604, as the name implies, is positioned in and/or passes through a patient's right atrium. The right atrial lead 604 optionally senses atrial cardiac signals and/or provides right atrial chamber stimulation therapy. As shown in FIG. 6, the IMD 102B is coupled to implantable right atrial lead 604 having, for example, an atrial tip electrode 620, which typically is implanted in the patient's right atrial appendage. The lead 604, as shown in FIG. 6, also includes an atrial ring electrode 621. Of course, lead 604 may have other electrodes as well. For example, the right atrial lead optionally includes a distal bifurcation having electrodes suitable for stimulation of autonomic nerves, non-myocardial tissue, other nerves, etc. In an alternative configuration, lead 610 can be replaced with a mechanism for connecting the IMD to various other devices. For example, the mechanism can facilitate connecting IMD 102B to a drug pump for dispensing drugs into the patient in accordance with instructions received from the IMD. The skilled artisan should recognize various other configurations that may be employed which are consistent with the principles described above and below.

To sense atrial cardiac signals, ventricular cardiac signals and/or to provide multi-site pacing therapy, particularly on the left side of a patient's heart, the IMD 102B is coupled to a coronary sinus lead 606 designed for placement in the coronary sinus and/or tributary veins of the coronary sinus.

Thus, the coronary sinus lead 606 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 606 is optionally designed to receive atrial and ventricular cardiac signals and to deliver left ventricular pacing therapy using, for example, at least a left ventricular tip electrode 622, left atrial pacing therapy using at least a left atrial ring electrode 624, and shocking therapy using at least a left atrial coil electrode 626. The coronary sinus lead 606 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

IMD 102B is also shown in electrical communication with the patient's heart 110 by way of an implantable right ventricular lead 608 having, in this exemplary implementation, a right ventricular tip electrode 628, a right ventricular ring electrode 630, a right ventricular (RV) coil electrode 632, and an SVC coil electrode 634. Typically, the right ventricular lead 608 is transvenously inserted into the heart 110 to place the right ventricular tip electrode 628 in the right ventricular apex so that the RV coil electrode 632 will be positioned in the right ventricle and the SVC coil electrode 634 will be positioned in the superior vena cava. Accordingly, the right ventricular lead 608 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

FIG. 7 shows an exemplary, simplified block diagram depicting various components of IMD 102B. The IMD 102B can be capable of treating both fast and slow arrhythmias with stimulation therapy, including cardioversion, defibrillation, and pacing stimulation. The IMD can be solely or further capable of sensing and/or delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable IMD. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 700 for IMD 102B is often referred to as the "can", "case" or "case electrode", and may be programmably selected to act as the return electrode for all "unipolar" modes. Housing 700 may further be used as a return electrode alone or in combination with one or more of the coil electrodes 626, 632 and 634 for shocking purposes. Housing 700 further includes a connector (not shown) having a plurality of terminals 701, 702, 704, 706, 708, 712, 714, 716, 718, 721 (shown schematically and, for convenience, the names of the electrodes to which they are connected are shown next to the terminals).

To achieve right atrial sensing and/or pacing, the connector includes at least a right atrial tip terminal ($A_R$ TIP) 701 adapted for connection to the atrial tip electrode 620. A right atrial ring terminal ($A_R$ RING) 702 is also shown, which is adapted for connection to the atrial ring electrode 621. To achieve left chamber sensing, pacing and/or shocking, the connector includes at least a left ventricular tip terminal ($V_L$ TIP) 704, a left atrial ring terminal ($A_L$ RING) 706, and a left atrial shocking terminal ($A_L$ COIL) 708, which are adapted for connection to the left ventricular tip electrode 622, the left atrial ring electrode 624, and the left atrial coil electrode 626, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 721).

To support right chamber sensing, pacing, and/or shocking, the connector further includes a right ventricular tip terminal ($V_R$ TIP) 712, a right ventricular ring terminal ($V_R$ RING) 714, a right ventricular shocking terminal (RV COIL) 716, and a superior vena cava shocking terminal (SVC COIL) 718, which are adapted for connection to the right ventricular tip electrode 628, right ventricular ring electrode 630, the RV coil electrode 632, and the SVC coil electrode 634, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 721).

At the core of the IMD 102B is a programmable microcontroller 720 that controls the various modes of stimulation therapy. As is well known in the art, microcontroller 720 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 720 includes the ability to process or monitor input signals (data or information) as controlled by a program code stored in a designated block of memory. The type of microcontroller is not critical to the described implementations. Rather, any suitable microcontroller(s) 720 may be used that carries out the functions described herein. The use of microprocessor-based control circuits for performing timing and data analysis functions are well known in the art.

FIG. 7 also shows an atrial pulse generator 722 and a ventricular pulse generator 724 that generate pacing stimulation pulses for delivery by the right atrial lead 604, the coronary sinus lead 606, and/or the right ventricular lead 608 via an electrode configuration switch 726. It is understood that in order to provide stimulation therapy in each of the four chambers of the heart the atrial and ventricular pulse generators, 722 and 724, may include dedicated, independent pulse generators, multiplexed pulse generators, or shared pulse generators. The pulse generators 722 and 724 are controlled by the microcontroller 720 via appropriate control signals 728 and 730, respectively, to trigger or inhibit the stimulation pulses.

Microcontroller 720 further includes a plurality of modules 732 that, when executed, perform various functions of the IMD. For instance, the modules can perform arrhythmia detection, timing control, capture detection, and/or morphology detection, among other functionalities.

The illustrated example specifically designates a timing control module 734, an arrhythmia detection module 736, a capture detection module 738, and a context recording module 740.

Timing control module 734 controls the timing of the stimulation pulses (e.g., pacing rate, atrio-ventricular (AV) delay, atrial interconduction (A-A) delay, or ventricular interconduction (VV) delay, etc.) as well as to keep track of the timing of refractory periods, blanking intervals, noise detection windows, evoked response windows, alert intervals, marker channel timing, etc., which is well known in the art.

The arrhythmia detection module 736 and the capture detection module 738 can be utilized by the IMD 102B for detecting patient conditions and determining desirable times to administer various therapies such as pacing, defibrillation and/or in vivo dispensing of pharmaceuticals.

The context recording module 740 provides a mechanism for recording a context in which biological data is sensed, such as by right atrial tip electrode 620, left ventricular tip electrode 622, and right ventricular tip electrode 628. The context recording module is operable to preserve contextual information in the form of supporting data with the respective sensed biological data. The context recording module 740 can obtain supporting data from various sources, such as the IMD's memory (described with specificity below). For example, information such as a model of IMD 1028, a serial number of the IMD, and/or various setting of the IMD can be stored in memory. In another example, the IMD may store patient clinical information, such as the patient's age and the patient's sex that can be accessed by the context recording module. Other supporting data can be obtained by the context recording module from various components of the IMD that may affect values of the sensed biological data. For instance, an analog-to-digital converter (described below) has various operational settings that can affect the sensed biological data values. Several other examples are described below.

In one manifestation, the context recording module 740 employs a watermark encoding module 741 to encode the supporting data as a watermark onto the sensed biological data to produce watermarked data. As described above in relation to FIGS. 2-5, the watermarking process can serve to encode the supporting data on the sensed biological data as a watermark in a manner that does not significantly diminish the usefulness of the sensed biological data. Further, the watermarking process can provide a security mechanism to the encoded data in that a 'key' is utilized to encode the supporting data with the sensed biological data. Practically speaking, only those in possession of the key can subsequently decode the watermark and access the supporting data.

In the illustrated configuration, the context recording module 740 is illustrated as a software/firmware logical component associated with microcontroller 720. In other scenarios, the context recording module could be a self-contained or standalone component, such as a hardware component that performs its own processing. The skilled artisan should recognize other configurations that are consistent with the concepts described above and below.

Electronic configuration switch 726 includes a plurality of switches for connecting the desired electrodes to the appropriate I/O circuits, thereby providing complete electrode programmability. Accordingly, switch 726, in response to a control signal 742 from the microcontroller 720, determines the polarity of the stimulation pulses (e.g., unipolar, bipolar, combipolar, etc.) by selectively closing the appropriate combination of switches (not shown) as is known in the art.

Atrial sensing circuits 744 and ventricular sensing circuits 746 may also be selectively coupled to the right atrial lead 604, coronary sinus lead 606, and the right ventricular lead 608, through the switch 726 for detecting the presence of cardiac activity (i.e., sensed biological data) in each of the four chambers of the heart. Accordingly, the atrial (ATR. SENSE) and ventricular (VTR. SENSE) sensing circuits, 744 and 746, may include dedicated sense amplifiers, multiplexed amplifiers, or shared amplifiers. Context recording module 740 can obtain some or all of the settings associated with these amplifiers as supporting data. Switch 726 determines the "sensing polarity" of the cardiac signal by selectively closing the appropriate switches, as is also known in the art. In this way, the clinician may program the sensing polarity independent of the stimulation polarity. The sensing circuits (e.g., 744 and 746) are optionally capable of obtaining information (i.e., sensed biological data) indicative of tissue capture.

Each sensing circuit 744 and 746 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 102B to deal effectively with the difficult problem of sensing the low amplitude signal characteristics of atrial or ventricular fibrillation. In such an instance, sensing the cardiac signal of interest generates sensed biological data. The various amplifier, gain control and bandpass filter settings can be supporting data that can be gathered by the context recording module 740 for encoding with the sensed biological data.

The outputs of the atrial and ventricular sensing circuits 744 and 746 are connected to the microcontroller 720, which, in turn, is able to trigger or inhibit the atrial and ventricular pulse generators 722 and 724, respectively, in a demand fashion in response to the absence or presence of cardiac activity in the appropriate chambers of the heart. Furthermore, as described herein, the microcontroller 720 is also capable of analyzing information output from the sensing circuits 744 and 746 and/or a data acquisition system (introduced below) to determine or detect whether capture has occurred and to program a pulse, or pulses, in response to such determinations. The sensing circuits 744 and 746, in turn, receive control signals over signal lines 748 and 750 from the microcontroller 720 for purposes of controlling the gain, threshold, polarization charge removal circuitry (not shown), and the timing of any blocking circuitry (not shown) coupled to the inputs of the sensing circuits, 744 and 746, as is known in the art.

For arrhythmia detection, IMD 102B utilizes the atrial and ventricular sensing circuits, 744 and 746, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals (i.e., sensed biological data) and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 736 of the microcontroller 720 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 752. The data acquisition system 752 is configured to acquire intracardiac electrogram (IEGM) signals, convert the raw analog data into a digital signal, and store the digital signals for later processing. The sensed cardiac signals can be thought of as sensed biological data whether the sensed cardiac signals are in analog or digital form. The data acquisition system 752 is coupled to the right atrial lead 604, the coronary sinus lead 606, the right ventricular lead 608 and/or the nerve or other tissue stimulation lead 610 through the switch 726 to sample cardiac signals across any pair of desired electrodes.

The microcontroller 720 is further coupled to a memory 760 by a suitable data/address bus(s) 762, wherein the programmable operating parameters (i.e., supporting data) used by the microcontroller 720 are stored and modified, as required, in order to customize the operation of the IMD 1028 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 110 within each respective tier of therapy.

Advantageously, operating parameters of the IMD 102B may be non-invasively programmed into the memory 760 through a telemetry circuit 764 in telemetric communication via communication link 766 with an external device 202, such as a programmer, transtelephonic transceiver, or a diagnostic system analyzer. The microcontroller 720 activates the telemetry circuit 764 with a control signal 768. The telemetry circuit 764 advantageously allows a signal or data (i.e., watermarked data) that includes both biological data and its supporting data as generated by context recording module 740 to be sent to the external device 202 through an established communication link 766. The watermarked data may be obtained directly from context recording module 740 or may have been previously generated by the context recording module 740 and be stored in memory 760.

The IMD 102B can further include a physiologic sensor(s) 770 to sense biological data including one or more of patient activity, patient posture, and respirations, among others. Microcontroller 720 can utilize data received from the physiologic sensor(s) 770 to adjust the various pacing parameters (such as rate, AV Delay, VV Delay, etc.) at which the atrial and ventricular pulse generators, 722 and 724, generate stimulation pulses. Information relating to physiologic sensor 770 can be included as supporting data by context recording module 740.

While shown as being included within the IMD 102B, it is to be understood that the physiologic sensor 770 may also be external to the IMD 102B, yet still be implanted within or carried by the patient. Examples of physiologic sensors that may be implemented in IMD 102B include known sensors that, for example, sense pressure, respiration rate, pH of blood, cardiac output, preload, afterload, contractility, oxygen levels, and so forth. Another sensor that may be used is one that detects activity variance, where an activity sensor is monitored to detect the low variance in the measurement corresponding to the sleep state and/or maintenance of a specific posture.

The physiological sensors 770 optionally include biological data sensors for detecting movement and minute ventilation in the patient. The physiological sensors 770 may include a position sensor and/or a minute ventilation (MV) sensor to sense minute ventilation, which is defined as the total volume of air that moves in and out of a patient's lungs in a minute. Sensed biological data generated by the position sensor and MV sensor are passed to the microcontroller 720 for analysis in determining whether to adjust the pacing rate, etc and/or for processing by context recording module 740.

The IMD 1026 optionally includes circuitry capable of sensing biological data in the form of heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator. The above mentioned accelerometer information can provide a commercially practicable example of accelerometer information that can be included in the supporting data in some implementations. Of course, each accelerometer has its own characteristics, some or all of which, can be conveyed in the supporting data along with setting of the individual device.

While an accelerometer may be included in the case of an IMD in the form of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

IMD 102B may also include, or be in communication with, an implanted drug pump 774 or other drug delivery mechanism to effect patient therapy. The drug pump can be activated in various scenarios, such as when a heart failure condition is detected by thoracic impedance/physiology correlation module 740.

The IMD 102B additionally includes a battery 776 that provides operating power to all of the circuits shown in FIG. 7. For the IMD 102B, which employs shocking therapy, the battery 776 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 776 also desirably has a predictable discharge characteristic so that elective replacement time can be detected.

The IMD 102B can further include magnet detection circuitry (not shown), coupled to the microcontroller 720, to detect when a magnet is placed over the IMD 102B. A magnet may be used by a clinician to perform various test functions of the IMD 102B and/or to signal the microcontroller 720 that the external device 202 is in place to receive or transmit data to the microcontroller 720 through the telemetry circuits 764.

The IMD 102B further includes an impedance measuring circuit 778 that is enabled by the microcontroller 720 via a control signal 780. The known uses for an impedance measuring circuit 778 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance, such as for determining shock thresholds, (HF indications—pulmonary edema and other factors); detecting when the device has been implanted; measuring stroke volume; and detecting the opening of heart valves, etc. The impedance measuring circuit 778 is advantageously coupled to the switch 726 so that any desired electrode may be used.

In the case where the IMD 102B is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 720 further controls a shocking circuit 782 by way of a control signal 784. The shocking circuit 782 generates shocking pulses in a range of joules, for example, conventionally up to about 40 J, as controlled by the microcontroller 720. Such shocking pulses are applied to the patient's heart 110 through at least two shocking electrodes, and as shown in this embodiment, selected from the left atrial coil electrode 626, the RV coil electrode 632, and/or the SVC coil electrode 634. As noted above, the housing 700 may act as an active electrode in combination with the RV electrode 632, or as part of a split electrical vector using the SVC coil electrode 634 or the left atrial coil electrode 626 (i.e., using the RV electrode as a common electrode).

Cardioversion level shocks are generally considered to be of low to moderate energy level (so as to minimize battery drain and the more rapid delivery of the shock if the lower energy levels are effective in restoring a normal rhythm), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 720 is capable of controlling the synchronous or asynchronous delivery of the shocking pulses.

In low-energy cardioversion, an IMD typically delivers a cardioversion stimulus (e.g., 0.1-5 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the IMD initiates defibrillation therapy.

While an IMD may reserve defibrillation as a latter tier therapy, it may use defibrillation as a first-tier therapy for VF. In general, an IMD does not synchronize defibrillation therapy with any given portion of an ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Operation

Figure 8:
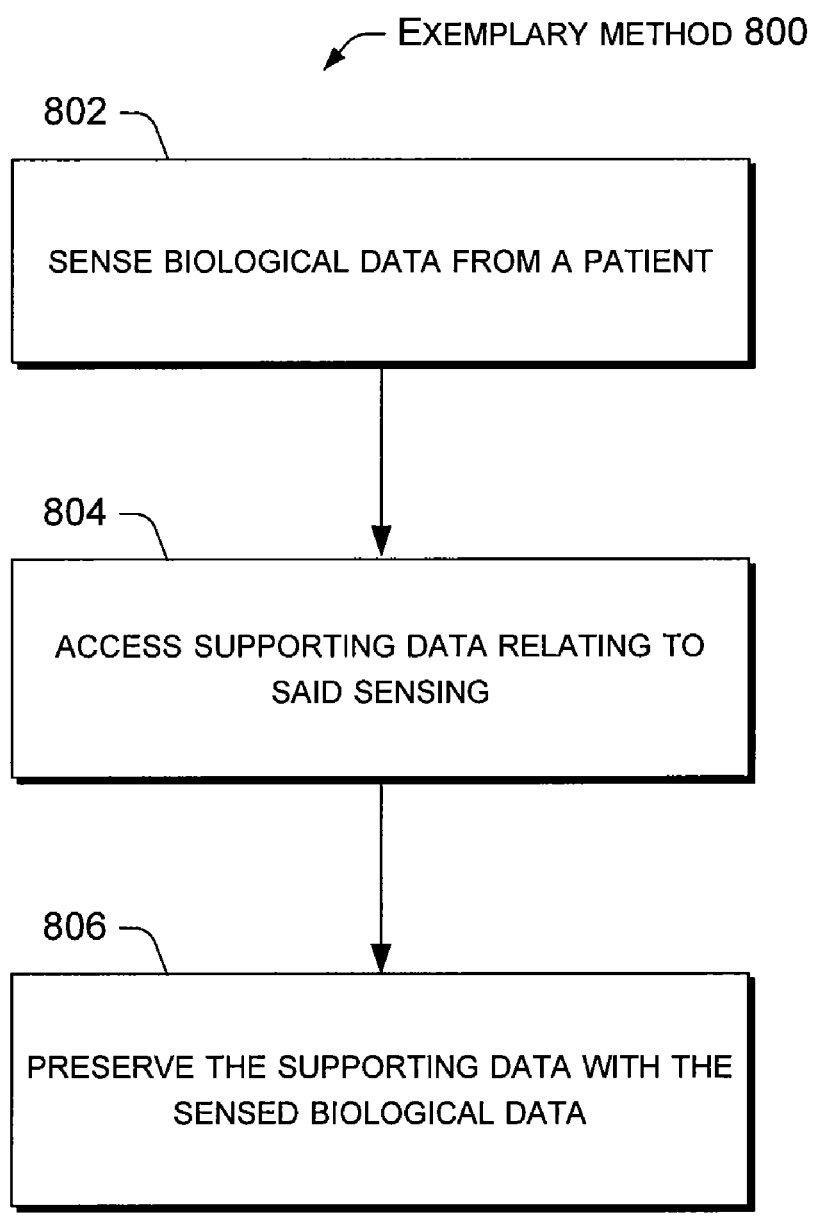
FIG. 8 is a block diagram of an exemplary technique for recording a context for sensed biological data in accordance with one implementation.

FIG. 8 shows an exemplary method or technique 800 for recording a context for sensed biological data. This method 800 may be implemented in connection with any suitably configured implantable medical devices (IMDs) and/or systems such as those described above in relation to FIGS. 1-7. Method 800 includes blocks 802-806. The order in which the method is described is not intended to be construed as a limitation, and any number of the described blocks can be combined in any order to implement the method, or an alternate method. Furthermore, the methods can be implemented in any suitable hardware, software, firmware, or combination thereof such that a computing device can implement the method. In one such instance, a computing device in the form of an IMD, implements some or all of the method. In another instance, an external computing device such as a programmer, implements some or all of the method.

At block 802, biological data is sensed from a patient. The biological data can be sensed or gathered by an IMD or other device configured to sense patient data. Examples of biological data are described above and can include data relating to cardiac function, respiratory function and/or neurological function, among others. The sensing can be performed by various sensors or devices. For instance, various sensors can be employed on, or in communication with, an implantable medical device (IMD) for sensing biological data. Examples of such sensors are described above in relation to FIGS. 1, 6, and 7.

At block 804, supporting data relating to the sensing of block 802 is accessed. Supporting data as used herein can include any information that can enhance the usefulness of the sensed biological data. The supporting data can be thought of as relating to a context in which the biological data was sensed. For instance, the supporting data can relate to information about the patient (i.e., patient clinical information) and/or to the devices that sensed the biological data. Any device that senses biological data influences values of the sensed biological data through one or both of design constraints and individual settings employed when the biological data is sensed. Other devices that don't directly sense the biological data but are involved in processing the sensed biological data also influence values of the sensed biological data. One such example described above in relation to FIG. 7 is an analog-to-digital converter. While the analog-to-digital converter is not directly involved in sensing the biological data, various algorithms and settings employed on the analog-to-digital converter affect values of the sensed biological data that is subsequently analyzed to determine a patient condition and to formulate a responsive patient therapy.

Supporting data can be accessed from various locations. In one example described above in relation to FIG. 7 supporting data is accessed from the IMD's memory and from other locations within or connected to the IMD such as specific components involved in sensing and/or processing the sensed biological data.

At block 806, the method preserves the supporting data with the sensed biological data. Preserving the supporting data with the sensed biological data serves to preserve the context (or a portion thereof) in which the biological data was sensed thereby enhancing the diagnostic value of the sensed biological data. Several examples are described above which serve to preserve the context. In one such example described in relation to FIG. 1, the supporting data is recorded with the sensed biological data, such as by embedding the supporting data on the biological data. FIGS. 2-5 describe a more detailed example where the recording is implemented via a watermark encoding technique. Utilizing watermarking to encode the supporting data onto the biological data offers several potential positive aspects. For instance, parameter values can be derived from the watermarked sensed biological data without decoding the watermark. Also, access to the supporting data can be controlled if desired.

In some scenarios, blocks 802-806 can all be completed by an IMD. In other cases, some or all of the blocks may be performed by other system components. For instance, an IMD can perform the sensing and transmit the sensed biological data to an external device which then accesses the supporting data, such as by requesting the supporting data from the IMD. The external device can then preserve the supporting data with the sensed biological data. Accomplishing all of blocks 802-806 on the IMD offers the potential advantage that a single data file can be generated at the point of sensing which contains both the sensed biological data and its supporting data. Then only the single data file is transmitted from the IMD to the external device thereby reducing risks of storing and transmitting separate data files. A further potential advantage of such a configuration is that transmission of a single data file can be advantageous since it is often more efficient to transmit a single data file as opposed to transmitting a separate data file for sensed biological data and transmitting another separate file for the supporting data. The single data file includes supporting data that is immediately useful for interpreting the sensed biological data and determining a patient therapy. Even if opened by a clinician years later, this single data file which preserves the sensing context with the sensed biological data greatly enhances the diagnostic value of that sensed biological data.

Conclusion

The concepts described above relate to recording a context in which biological data was sensed with the sensed biological data to enhance the diagnostic value of the sensed biological data. The implementations and examples described herein should allow the skilled artisan to recognize other manifestations of these concepts. Therefore, although exemplary techniques, methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An implantable medical device (IMD) comprising:
   a mechanism sensing biological data from a patient;
   a pseudo-noise generating mechanism that generates a pseudo-noise sequence, wherein the sequence is a relatively constant low-energy signal throughout the frequency spectrum except near the lowest frequencies; and
   a mechanism embedding supporting data on the sensed biological data in a single data file, wherein the mechanism embedding supporting data combines the supporting data with the pseudo-noise sequence to generate a pseudo-noise signal that is embedded on the sensed biological data and the supporting data is encoded as binary data having bits of the binary data divided into multiple supporting data fields.

2. The IMD of claim 1, wherein the mechanism embedding supporting data encodes the supporting data on the biological data.

3. The IMD of claim 1, wherein the mechanism embedding supporting data encodes the supporting data on the biological data as a digital watermark.

4. The IMD of claim 1, wherein the mechanism embedding supporting data employs a digital key to generate the pseudo-noise sequence so that subsequent access to the embedded supporting data requires possession of the digital key.

5. The IMD of claim 1, wherein the mechanism embedding supporting data employs a security mechanism operable to restrict access to the embedded supporting data.

6. The IMD of claim 5, wherein the security mechanism employs a key that is required to access the embedded supporting data.

7. The IMD of claim 1, wherein the supporting data comprises one or more of: an IMD model number, an IMD serial number, IMD configuration data, a sensor mechanism model number, a sensor mechanism serial number, and patient clinical data.

8. The IMD of claim 1, wherein the mechanism embedding supporting data comprises a context recording module that records contextual information about the sensing of the sensed biological data.

9. The IMD of claim 1, wherein the IMD comprises at least one amplifier and at least one lead and wherein the supporting data fields comprises amplifier gain settings of the at least one amplifier, amplifier filter settings of the at least one amplifier, and lead configurations of the at least one lead.

10. An implantable medical device (IMD) comprising:
    means for sensing biological data from a patient, wherein the means for sensing comprises at least one electrode for positioning in electrical contact with a patient tissue and an analog-to-digital converter for converting biological data sensed by the at least one electrode into digital data in accordance with at least one parameter setting of the IMD;
    means for obtaining supporting data;
    means for generating a pseudo-noise sequence comprising a context recording module operable to combine the supporting data with the pseudo-noise sequence to generate a pseudo-noise signal, wherein the means for generating the pseudo-noise sequence generates a relatively constant low-energy signal throughout the frequency spectrum except near the lowest frequencies;
    means for embedding the supporting data upon the sensed biological data by embedding the pseudo-noise signal upon the sensed biological data as a digital watermark; and
    means for generating a data file containing the sensed biological data embedded with the supporting data.

11. The IMD of claim 10, wherein the at least one parameter setting comprises a sensitivity parameter setting.

12. The IMD of claim 11, wherein the means for generating is operable to include the sensitivity parameter setting in the supporting data.

13. The IMD of claim 10, wherein the means for generating comprises a microcontroller including a watermark encoding module.

14. The IMD of claim 10, wherein the IMD comprises at least one means for amplifying and at least one means for filtering and wherein at least one parameter setting comprises an amplification parameter of the at least one means for amplifying or a filter characteristic of the at least one means for filtering.

15. A computer-implemented method comprising:
    sensing biological data from a patient;
    accessing supporting data relating to said sensing; and
    embedding the supporting data on the sensed biological data, wherein the embedding is performed on portions of the sensed biological data from which substantially no parameter values are derived and which are of less prognostic value than the other portions of the sensed biological data.

16. The computer-implemented method as recited in claim 15, wherein the sensing comprises receiving the patient data from a sensing device that sensed the patient data.

17. The computer-implemented method as recited in claim 15, wherein the accessing further comprises accessing, from a memory of an implantable medical device (IMD) supporting data relating to patient clinical data comprising one or more of: patient age and patient sex.

18. The computer-implemented method as recited in claim 15, wherein the embedding comprises encoding the supporting data onto the sensed biological data as a digital watermark.

19. The computer-implemented method as recited in claim 15, wherein the embedding comprises combining the supporting data with a pseudo-noise sequence as a pseudo-noise signal that is encoded on the sensed biological data.

20. The computer-implemented method as recited in claim 15, wherein the embedding comprises encoding the supporting data on the sensed data with a key so that subsequent access to the encoded supporting data requires possession of the key.

21. The computer-implemented method as recited in claim 15, wherein the embedding is accomplished on an implantable medical device implanted in a patient; and
further comprising conveying the sensed biological data with the embedded supporting data to an external device.

22. The computer-implemented method as recited in claim 15, wherein the sensing and accessing are accomplished on an implantable medical device and wherein the embedding is accomplished by another device that is external to the patient.

23. The computer-implemented method as recited in claim 15, further comprising obtaining the supporting data from the sensed biological data embedded with the supporting data by sending the sensed biological data embedded with the supporting data through a low pass filter.

* * * * *